(12) United States Patent
Drevelle et al.

(10) Patent No.: US 8,716,496 B2
(45) Date of Patent: May 6, 2014

(54) SULFONATED COUMARINS, THEIR SYNTHESIS, FLUOROGENIC SUBSTRATES RESULTING FROM GRAFTING OF THESE COUMARINS ON SUGARS, METHOD FOR OBTAINING THESE SUBSTRATES, AND THEIR APPLICATIONS

(75) Inventors: Antoine Drevelle, Fontaine Macon (FR); Sylvain Ladame, London (GB); Majdi Najah, Fontaine Macon (FR); Estelle Mayot, Strasbourg (FR)

(73) Assignees: Ets J. Soufflet, Nogent-sur-seine (FR); Universite de Strasbourg, Strasbourg (FR)

( * ) Notice: Subject to any disclaimer, the term of this patent is extended or adjusted under 35 U.S.C. 154(b) by 0 days.

(21) Appl. No.: 13/823,294

(22) PCT Filed: Sep. 16, 2011

(86) PCT No.: PCT/FR2011/000504
§ 371 (c)(1),
(2), (4) Date: Mar. 20, 2013

(87) PCT Pub. No.: WO2012/038614
PCT Pub. Date: Mar. 29, 2012

(65) Prior Publication Data
US 2013/0183700 A1    Jul. 18, 2013

(30) Foreign Application Priority Data
Sep. 21, 2010  (FR) ..................... 10 03759

(51) Int. Cl.
*C07D 311/78*    (2006.01)
*C12Q 1/34*    (2006.01)
*C07H 15/24*    (2006.01)

(52) U.S. Cl.
USPC ............. 549/280; 549/289; 435/18; 536/18.1

(58) Field of Classification Search
USPC ................ 549/280, 289; 536/18.1; 435/18
See application file for complete search history.

(56) References Cited

U.S. PATENT DOCUMENTS 5,830,912 A * 11/1998 Gee et al. ............... 514/457

FOREIGN PATENT DOCUMENTS

GB    2 319 250 A    5/1998

*Primary Examiner* — Susan Hanley
*Assistant Examiner* — Paul Martin
(74) *Attorney, Agent, or Firm* — Oliff PLC

(57) ABSTRACT

Substituted sulfonated coumarins are expressed in the general formula (I), where: $R^1$ is H, OH, or a substituted or unsubstituted, straight or branched $C_1$-$C_6$ alkyl radical, or —$COR^4$, or —$COOR^4$, or —$CONHR^4$, $R^2$ is H or a halogen, in particular fluorine, or a substituted or unsubstituted, straight or branched $C_1$-$C_6$ alkyl radical, or —$COR^4$, or —$COOR^4$, or —$CONHR^4$, $R^1$ and $R^2$ being capable of together forming a ring, such as a substituted or unsubstituted aryl or furane, $R^3$ is H or a halogen, in particular fluorine, or a substituted or unsubstituted, straight or branched $C_1$-$C_6$ alkyl radical, or —$COR^4$, or —$COOR^4$, or —$CONHR^4$, where $R^4$ is H, or a substituted or unsubstituted, straight or branched $C_1$-$C_6$ alkyl radical, or a substituted or unsubstituted aryl, and M is Na or K.

14 Claims, 6 Drawing Sheets

Formula (I)

SULFONATED COUMARINS, THEIR SYNTHESIS, FLUOROGENIC SUBSTRATES RESULTING FROM GRAFTING OF THESE COUMARINS ON SUGARS, METHOD FOR OBTAINING THESE SUBSTRATES, AND THEIR APPLICATIONS

TECHNICAL FIELD

The present invention relates to sulfonated coumarins, their synthesis, fluorogenic substrates resulted from grafting of these coumarins on sugars, to the method for obtaining these substrates, as well as to their applications.

BACKGROUND

Different methods for making such sulfonated coumarins are known, for example by the British patent GB 9 723 365 in the name of MOLECULAR PROBES which describes the synthesis of derivatives of 6,8-difluoro-7-hydroxycoumarin.

Thus, this patent notably mentions sodium 6,8-difluoro-7-hydroxycoumarin-4-methanesulfonate (compound no. 37).

Patent GB 9 723 365 also describes compounds resulting from a replacement of the hydroxyl group with a sugar remainder, the latter being therefore grafted on sulfonated coumarin. The reproduction of the grafting method described in the aforementioned patent is not valid for sulfonated coumarins since they are not soluble under the described conditions.

SUMMARY

A goal of the present invention is to synthesize novel substituted sulfonated coumarins.

Another goal of the present invention is to provide fluorogenic substrates resulting from the grafting of substituted sulfonated coumarins on sugars by a reproducible grafting method with different sugars and different substituted sulfonated coumarins. In the present description, by fluorogenic substrate is meant a non-fluorescent substrate, for which hydrolysis of the bond between the sugar and the coumarin releases the coumarin, which is fluorescent per se.

Another goal of the present invention relates to a method for detecting glycosidase activities (EC3.2.1) on enzymatic extracts, either purified or not, or on microorganisms or on cells.

More specifically, the present invention relates to a family of substituted sulfonated coumarins of general formula (I)

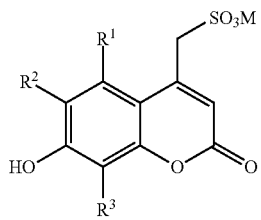

wherein:
R$^1$ represents H, or OH, or a linear or branched C$_1$-C$_6$ alkyl radical, either substituted or not, or —COR$^4$, or —COOR$^4$, or —CONHR$^4$ R$^2$ represents H, or a halogen, notably fluorine, or a linear or branched C$_1$-C$_6$ alkyl radical, either substituted or not, or —COR$^4$, or —COOR$^4$, or —CONHR$^4$ R$^1$ and R$^2$ may form together a ring, such as an aryl or a furane, either substituted or not —R$^3$ represents H, or a halogen, notably fluorine, or a linear or branched C$_1$-C$_6$ alkyl radical, either substituted or not, or —COR$^4$, or —COOR$^4$, or —CONHR$^4$ with R$^4$ being H, or a linear or branched C$_1$-C$_6$ alkyl radical, either substituted or not, or an aryl, either substituted or not M represents Na or K The present invention also relates to novel substrates having the general formula (II)

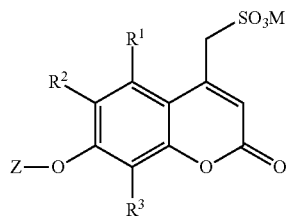

wherein:
R$^1$ represents H, or OH, or a linear or branched C$_1$-C$_6$ alkyl radical, either substituted or not, or —COR$^4$, or —COOR$^4$, or —CONHR$^4$ R$^2$ represents H, or a halogen, notably fluorine, or a linear or branched C$_1$-C$_6$ alkyl radical, either substituted or not, or —COR$^4$, or —COOR$^4$, or —CONHR$^4$ R$^1$ and R$^2$ may form together a ring, such as an aryl or a furane, either substituted or not —R$^3$ represents H, or a halogen, notably fluorine, or a linear or branched C$_1$-C$_6$ alkyl radical, either substituted or not, or —COR$^4$, or —COOR$^4$, or —CONHR$^4$ with R$^4$ being H, or a linear or branched C$_1$-C$_6$ alkyl radical, either substituted or not, or an aryl, either substituted or not M represents Na or K Z represents a sugar selected from the following sugars: cellobiose, xylobiose, maltose, saccharose, glucose, xylose, galactose, arabinose, xylan, glucan, xylotriose, maltotriose, cellotriose, xylotetraose or a mixture of some of them.

DETAILED DESCRIPTION OF THE EMBODIMENTS

Figure 1:
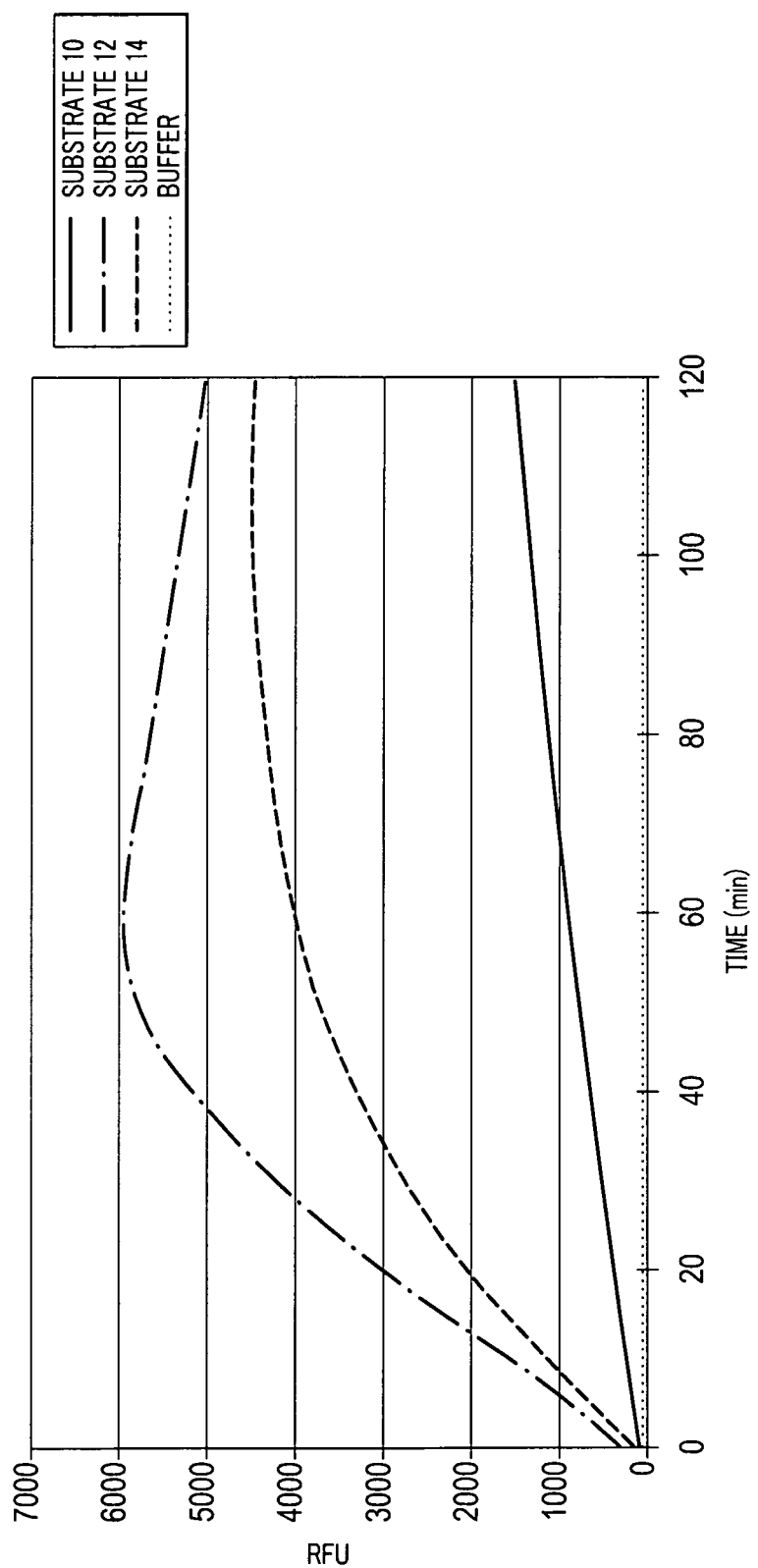
FIG. 1 shows detection of enzymatic activities on the soluble extract of enzymes A with the substrates 10, 12, and 14.

The invention will be better understood upon reading the description which follows, reference being made to the following compounds numbered from 1-24:

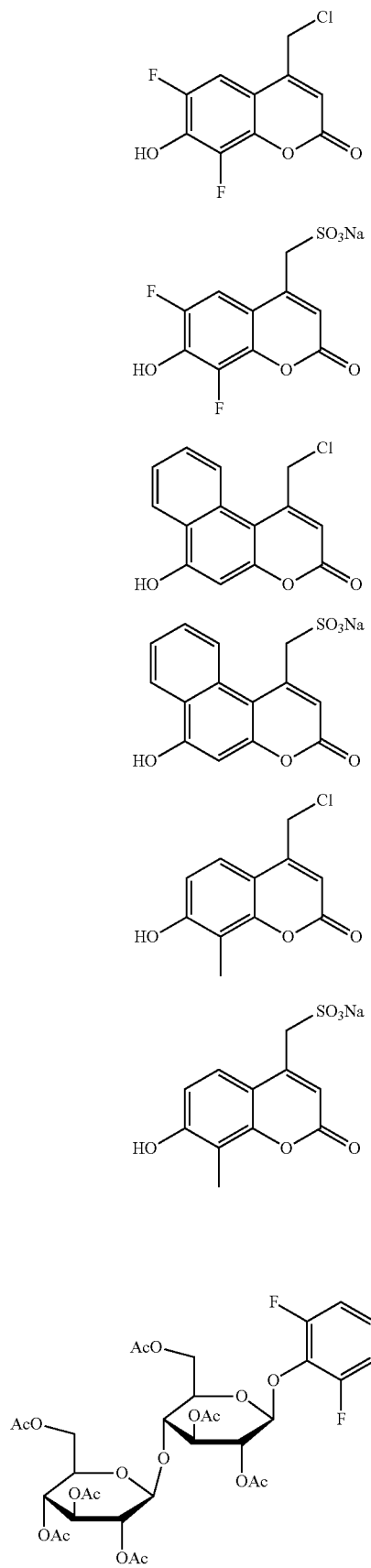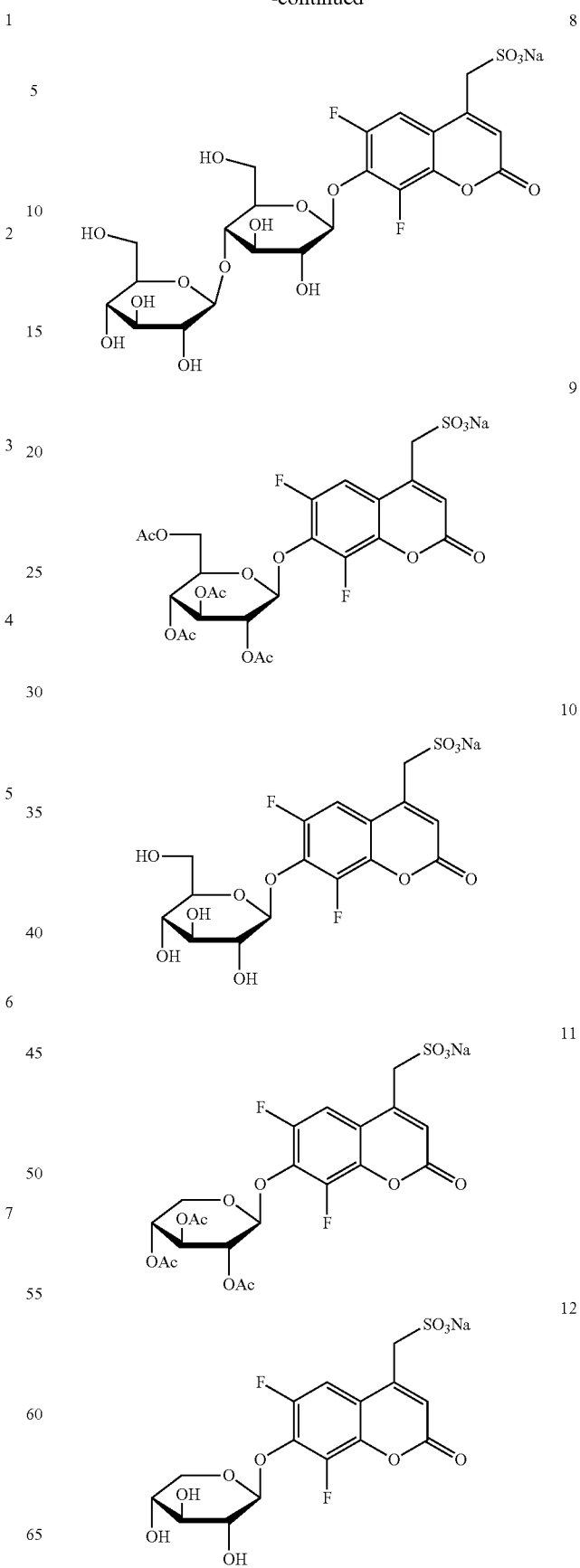

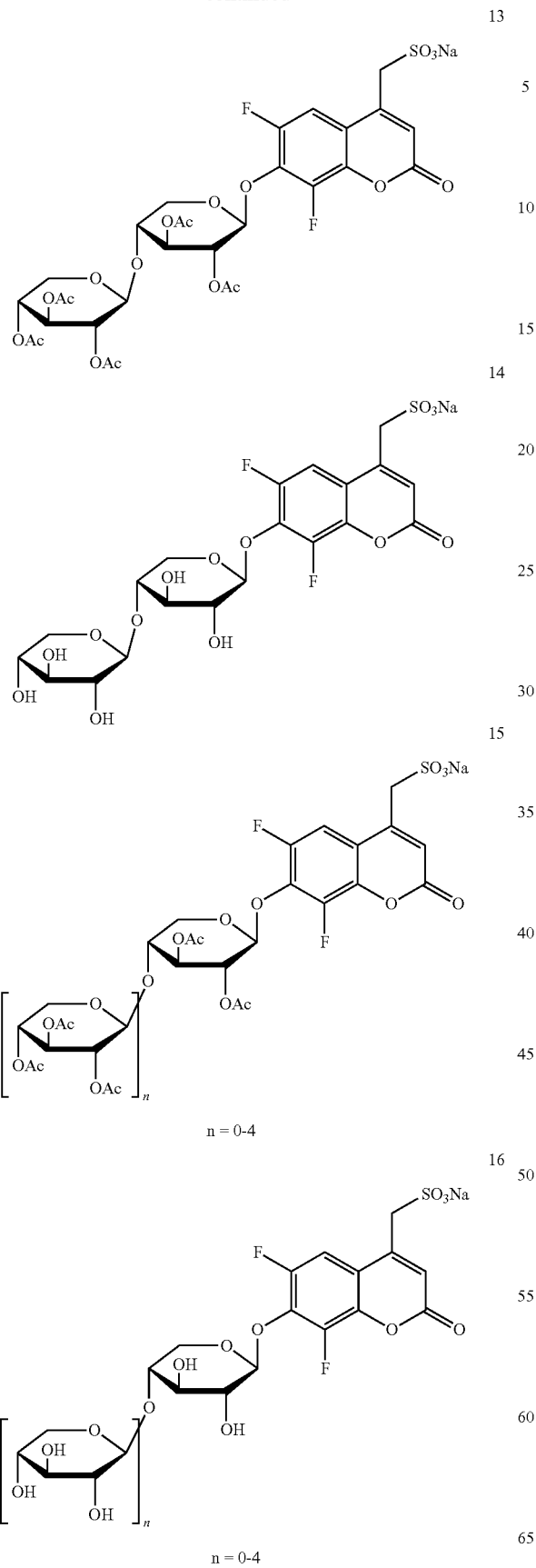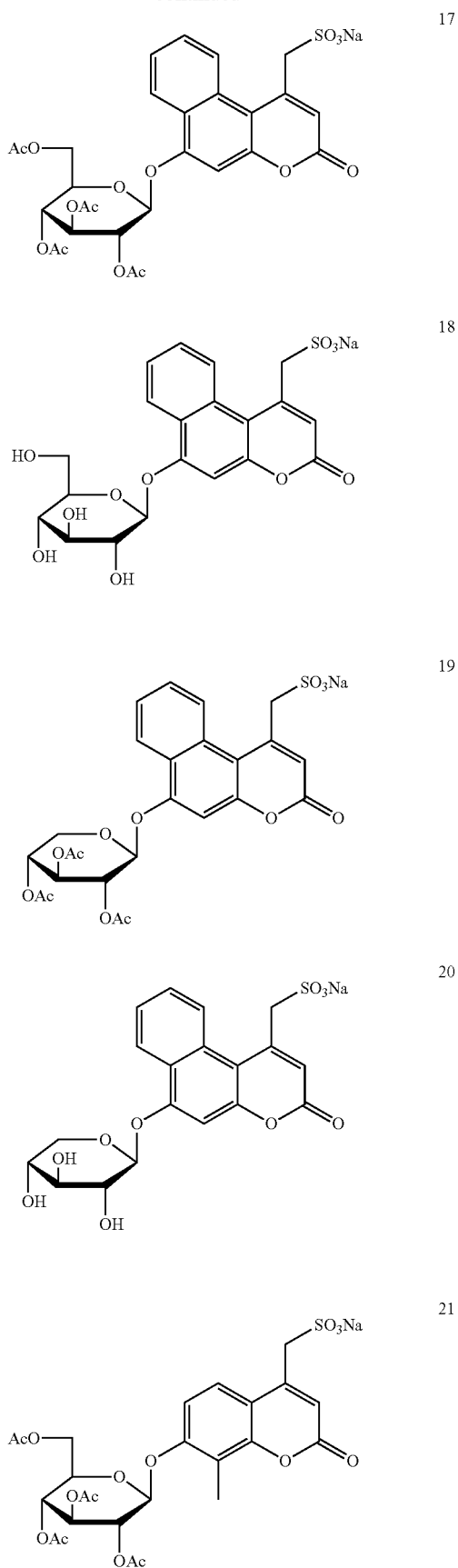

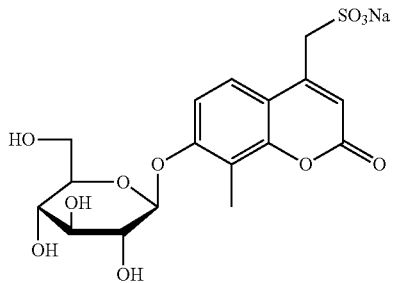

22

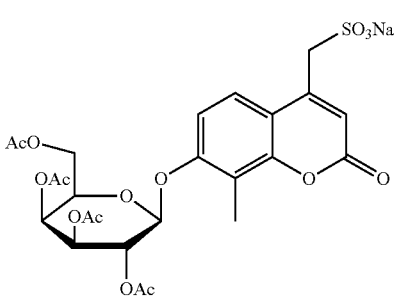

23

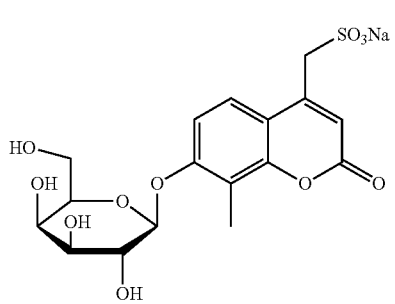

24 among which the compounds 2, 4 and 6 are substituted sulfonated coumarins entering the general formula (I) and wherein the compounds 8, 10, 12, 14, 16, 18, 20, 22 and 24 are examples of substrates entering the general formula (II).

Different examples of synthesis of these coumarins and of substrates will now be given, as an indication and by no means as a limitation.

Example 1

Synthesis of 4-chloromethyl-6,8-difluoro-7-hydroxycoumarin (1)

A solution of 2,4-difluororesorcinol (0.8 g) in 8 mL of methyl sulfonic acid is introduced into a flask and then 1.3 equivalents (963 µL) of ethyl 4-chloroacetoacetate are added dropwise. After 3 hours of stirring at room temperature, the mixture is cooled to 0° C. and then 100 mL of water are added. The residue is then filtered, dried and washed with diethyl ether in order to obtain 0.34 g (25%) of the compound 1.

$^1$H NMR (MeOD) δ (ppm) 7.42 (d, 1H); 6.05 (s, 1H); 4.81 (s, 2H).

Example 2

Synthesis of sodium 6,8-difluoro-7-hydroxycoumarin-4-methanesulfonate (2)

A solution of 320 mg of the compound 1 dissolved in 25 mL of ethanol is introduced into a flask, and then a solution of sodium sulfite (1.1 equivalents, 185 mg) in 6 mL of water is added. The mixture is refluxed and the development of the reaction is followed by TLC (Thin Layer Chromatography). After 40 hours of heating, the mixture is cooled to 0° C. The solution is filtered and the filtrate is then evaporated under reduced pressure in order to obtain a yellow solid.

The obtained solid is purified once by reverse phase chromatography on a pre-packed silica column (eluent: pure water, cartridge PURIFLASH INTERCHROM C18) and then subsequently with a purification apparatus BIOTAGE-ISOLERAONE (eluent: pure water, cartridge SNAP C18 120 g, elution flow rate: 25 mL/min).

After evaporation of the water under reduced pressure, the product 2 is obtained pure with a yield of 40%.

$^1$H NMR (D$_2$O) δ (ppm) 7.28 (d, 1H); 6.18 (s, 1H); 4.32 (s 2H).

$^{13}$C NMR (D$_2$O) δ (ppm) 163.7; 153.1 (dd); 150.5 (t); 149.0; 142.2 (dd); 140.7 (m); 109.2; 105.3 (d); 103.6 (d); 52.7.

Maximum excitation/emission=370/470 nm (10 µM in 50 mM phosphate buffer, NaCl 150 mM, pH=7.5).

Example 3

Synthesis of 5,6-benzo-4-chloromethyl-7-hydroxycoumarin (3)

A solution of 1,3-dihydroxynaphthalene (1 g) in 10 mL of methane sulfonic acid is introduced into a flask and then 1.3 equivalents (1.10 ml) of ethyl 4-chloroacetoacetate are added dropwise. After 4 days of stirring at room temperature, the mixture is cooled to 0° C. and then 50 mL of water are added. The residue is then filtered, washed with water and dried in order to obtain 1.30 g (80%) of the compound 3.

$^1$H NMR (DMSO) δ (ppm) 8.47 (d, 1H); 8.32 (d, 1H); 7.75 (t, 1H); 7.60 (t, 1H); 6.88 (s, 1H); 6.58 (s, 1H); 5.33 (s, 2H).

Example 4

Synthesis of sodium 5,6-benzo-7-hydroxycoumarin-4-methanesulfonate (4)

A solution of 0.7 g of the compound 3 dissolved in 50 mL of ethanol is introduced into a flask, and then a solution of sodium sulfite (1.1 equivalents, 370 mg) in 13 mL of water is added. The mixture is refluxed and the development of the reaction is followed by TLC. After 20 hours of heating, the mixture is cooled to 0° C. The solution is filtered on a Büchner funnel and the filtrate is then evaporated under reduced pressure in order to obtain the crude compound 4 in the form of a yellow solid with a yield of 77%.

The obtained solid is purified once by reverse phase chromatography on a pre-packed silica column (eluent: pure water, cartridge PURIFLASH INTERCHROM C18) and then subsequently with a purification apparatus BIOTAGE-ISOLERAONE (eluent: 10% acetonitrile/90% water, cartridge SNAP C18 120 g, elution flow rate: 25 mL/min).

After evaporation of the solvents under reduced pressure, the product 4 is obtained pure with a yield of 31%.

$^1$H NMR (D$_2$O) δ (ppm) 8.26 (d, 1H); 8.02 (d, 1H); 7.56 (t, 1H); 7.44 (t, 1H); 6.32 (s, 1H); 6.11 (s, 1H); 4.45 (s, 2H).

Maximum excitation/emission=420/510 nm (100 µM in 50 mM phosphate buffer, NaCl 150 mM, pH=7.5).

Example 5

Synthesis of 4-chloromethyl-7-hydroxy-8-methylcoumarin (5)

A solution of 2-methylresorcinol (1 g) in 10 mL of methyl sulfonic acid is introduced into a flask and then 1.3 equivalents (1.42 ml) of ethyl 4-chloroacetoacetate are added dropwise. After 1 night of stirring at room temperature, the mixture is cooled to 0° C. and then 50 mL of water are added. The residue is then filtered, dried and washed with diethyl ether in order to obtain 1.63 g (90%) of the compound 5.

$^1$H NMR (DMSO) δ (ppm) 7.52 (d, 1H); 6.90 (d, 1H); 6.41 (s, 1H); 4.93 (s, 2H); 2.16 (s, 3H).

$^{13}$C NMR (DMSO) δ (ppm) 160.8; 159.7; 153.6; 151.7; 123.5; 112.3; 111.6; 111.1; 109.8; 41.9; 8.4.

Example 6

Synthesis of sodium 4-chloromethyl-7-hydroxy-8-methylcoumarin-4-methanesulfonate (6)

A solution of 1 g of the compound 5 dissolved in 90 mL of ethanol is introduced into a flask, and then a solution of sodium sulfite (1.1 equivalents, 617 mg) in 22 mL of water is added. The mixture is refluxed. After 20 hours of heating, the mixture is cooled to 0° C. The solution is filtered on a Büchner funnel, the obtained beige residue is washed with ethanol, as for the filtrate, it is evaporated under reduced pressure in order to obtain a yellow solid. This solid is washed with ethanol and diethyl ether. Both obtained solids are collected in order to obtain 1 g (80%) of the crude compound 6.

The crude compound 6 is then purified with several successive reverse phase chromatographies on a pre-packed silica column (eluent: pure water, cartridge PURIFLASH INTERCHROM C18) in order to obtain the pure product 6 with a yield of 23%.

$^1$H NMR (D$_2$O) δ (ppm) 7.32 (d, 1H); 6.69 (d, 1H); 6.15 (s, 1H); 4.19 (s, 2H); 1.97 (s, 3H).

$^{13}$C NMR (D$_2$O) δ (ppm) 164.2; 158.5; 148.9; 123.9; 112.6; 112.2; 111.8; 111.3; 52.4; 7.3.

Maximum excitation/emission=340/485 nm (10 µM in 50 mM phosphate buffer, NaCl 150 mM, pH=7.5).

Example 7

Synthesis of the sodium β-D-cellobioside 6,8-difluoro-7-hydroxycoumarin-4-methanesulfonate substrate (8)

Bromination of the Protected Sugar:

Under a nitrogen atmosphere, 1 g of aceto-α-D-cellobiose and 12.5 mL of anhydrous DCM (dichloromethane) are introduced into a flask. The mixture is cooled to 0° C. and then 15 mL of a hydrobromic acid solution in solution at 33% in acetic acid are added dropwise. After 5 hours of reaction at 0° C., 25 mL of DCM are added, and then the mixture is further stirred for 10 mins. A solution of potassium carbonate is then added carefully until evolvement of CO$_2$ disappears, the medium is left with stirring for 20 mins. After decantation, the organic phase is recovered, the aqueous phase is extracted three times with DCM, and then the organic phases are combined, dried on MgSO$_4$ and evaporated under reduced pressure. The acetobromo-α-D-cellobiose is obtained as a white solid with a yield of 62%. The thereby obtained product is unstable, and it should either be used directly, or kept at −20° C.

$^1$H NMR (CDCl$_3$) δ (ppm) 6.67 (m, 1H); 5.55 (t, 1H); 5.13 (m, 2H); 4.95 (t, 1H); 4.78 (m, 1H); 4.55 (m, 2H); 4.38 (m, 1H); 4.20 (m, 2H); 4.07 (m, 1H); 3.84 (m, 1H); 3.68 (m, 1H); 2.09 (m, 21H).

Grafting the Sugar on the Coumarin:

Under a nitrogen atmosphere and protected from light, 40 mg of coumarin 2 diluted in 5 mL of anhydrous DMF (dimethylformamide) and 150 mg of silver carbonate are introduced into a flask. 4 equivalents of acetobromo-α-D-cellobiose (350 mg) are dissolved in 10 mL of anhydrous DMF. This solution is then very slowly added to the previous mixture. After one night of stirring at room temperature, the solution is filtered on celite and the filtrate is evaporated under reduced pressure.

The obtained solid is finally purified by chromatography on a silica column (eluent: 20% MeOH/80% DCM). The compound 7 is obtained with a yield of 4.8%.

Deprotection of the Functions of the Acetal Type:

Under a nitrogen atmosphere, 40 mg of the compound 7 and 7.5 mL of anhydrous methanol are introduced into a flask. The mixture is cooled to 0° C. and then a solution of 16 mg of sodium methylate in 5 mL of methanol is added dropwise. The development of the reaction is followed by LC/MS. After 1 hour of stirring, the medium is neutralized by adding a diluted solution of citric acid. After further stirring for 20 mins, the solvent is evaporated under reduced pressure in order to obtain a translucent yellow oil.

The obtained residue is purified once by reverse phase chromatography on a pre-packed silica column (eluent: pure water, cartridge PURIFLASH INTERCHROM C18) and then subsequently by HPLC (High-Pressure Liquid Chromatography).

HPLC method: 0 min→10 min; 1.5 mL/min: 100% water
10 min→19 min; 1.5 mL/min: 90% eau/10% acetonitrile
19 min→23 min; 1.5 mL/min: 100% acetonitrile
23 min→25 min; 1.5 mL/min: 100% water Characteristics of the column: Hypersil Column; Gold Phenyl; Thermofisher 5; length 250 mm; diameter 4.6 mm.

The injections are of 80 µL and the product only flows out into the water phase in the interval: 0 min→10 min, then closely followed by the free coumarin present in solution.

After freeze drying, the product 8 is obtained pure as a white solid with a yield of 30%.

$^1$H NMR (D$_2$O) δ (ppm) 7.55 (d, 1H); 6.60 (s, 1H); 5.17 (d, 1H); 4.45 (d, 1H); 4.38 (s, 2H); 3.9-3.2 (m, 12H).

Example 8

Synthesis of the sodium β-D-glucoside 6,8-difluoro-7-hydroxycoumarin-4-methanesulfonate substrate (10)

Grafting the Sugar on the Coumarin:

Under a nitrogen atmosphere and protected from light, 100 mg of coumarin 2 diluted in 5 mL of anhydrous DMF and 5 equivalents of silver carbonate are introduced into a flask. 5 equivalents of acetrobromo-α-D-glucose are dissolved in 5 mL of anhydrous DMF. This solution is then added very slowly to the previous mixture. The development of the reaction is followed by LC/MS. After stirring overnight at room temperature, the solution is filtered on celite and the filtrate is evaporated under reduced pressure.

The obtained solid is finally purified by chromatography on a silica column (eluent: 20% MeOH/80% DCM). The compound 9 is obtained with a yield of 37%.

$^1$H NMR (MeOD) δ (ppm) 7.73 (d, 1H); 6.63 (s, 1H); 5.4-5.1 (m, 4H); 4.4-4.1 (m, 2H); 4.34 (s, 2H); 4.04 (m, 1H); 2.1 (m, 12H).

Deprotection of the Functions of the Acetal Type:

Under a nitrogen atmosphere, 45 mg of the compound 9 and 10 mL of anhydrous methanol are introduced into a flask. The mixture is cooled to 0° C. and then 350 µL of a 1% (g/g) sodium methylate solution in methanol is added dropwise. The development of the reaction is followed by LC/MS. After 2 h 30 mins of stirring, some AMBERLITE IR120 is added until neutralization of the medium. After filtration of the AMBERLITE, the filtrate is evaporated under reduced pressure.

The obtained residue is purified once by reverse chromatography on a pre-packed silica column (eluent: pure water, cartridge PURIFLASH INTERCHROM C18) and then subsequently with a purification apparatus BIOTAGE-ISOLERAONE (eluent: pure water, cartridge SNAP C18 12 g, elution flow rate: 5 mL/min).

After freeze drying the product 10 is obtained pure with a yield of 54%.

$^1$H NMR (D$_2$O) δ (ppm) 7.52 (d, 1H); 6.54 (s, 1H); 5.11 (d, 1H); 4.32 (s, 2H); 3.78 (m, 1H); 3.63 (m, 1H); 3.6-3.4 (m, 4H).

Example 9

Synthesis of the sodium β-D-xyloside 6,8-difluoro-7-hydroxycoumarin-4-methanesulfonate substrate (12)

Bromination of the Protected Sugar:

Under a nitrogen atmosphere, 500 mg of aceto-β-D-xylopyranose and 10 mL of DCM are introduced into a flask. The mixture is cooled to 0° C. and then 5 equivalents of hydrobromic acid in solution at 33% in acetic acid are added dropwise. After 24 hours of reaction, 15 mL of DCM are added, the mixture is cooled to 0° C. and then 20 mL of ice water are added. After separation of both phases, the organic phase is washed three times with a saturated NaHCO$_3$ solution and three times with water. After drying on MgSO$_4$ and filtration, the filtrate is evaporated under reduced pressure. The obtained acetobromo-α-D-xylose is then directly introduced into the next step.

Grafting of the Sugar on the Coumarin:

Under a nitrogen atmosphere and protected from light, 100 mg of coumarin 2 diluted in 8 mL of anhydrous DMF and 5 equivalents of silver carbonate are introduced into a flask. 5 equivalents of acetrobromo-α-D-xylose are dissolved in 6 mL of anhydrous DMF. This solution is then added very slowly to the previous mixture. The development of the reaction is followed by LC/MS. After one night of stirring at room temperature, the solution is filtered on celite and the filtrate is evaporated under reduced pressure.

The obtained solid is finally purified by chromatography on a silica column (eluent: 20% MeOH/80% DCM). The compound 11 is obtained pure with a yield of 34%.

$^1$H NMR (MeOD/D$_2$O) δ (ppm) 7.70 (d, 1H); 6.66 (s, 1H); 5.46 (d, 1H); 5.25 (m, 2H); 5.04 (m, 1H); 4.37 (s, 2H); 4.32 (m, 1H); 3.70 (m, 1H); 2.13 (m, 9H).

Deprotection of the Functions of the Acetal Type:

Under a nitrogen atmosphere, 62 mg of the compound 11 and 15 mL of anhydrous methanol are introduced into a flask. The mixture is cooled to 0° C. and then 500 µL of a 1% (g/g) sodium methylate solution in methanol is added dropwise. The development of the reaction is followed by LC/MS. After 1 h 30 mins of stirring, some AMBERLITE IR120 is added until neutralization of the medium. After filtration of the AMBERLITE, the filtrate is evaporated under reduced pressure.

The obtained residue is purified once by reverse chromatography on a pre-packed silica column (eluent: pure water, cartridge PURIFLASH INTERCHROM C18) and then subsequently with a purification apparatus BIOTAGE-ISOLERAONE (eluent: pure water, cartridge SNAP C18 30 g, elution flow rate: 15 mL/min).

After freeze drying, the product 12 is obtained pure with a yield of 62%.

$^1$H NMR (D$_2$O) δ (ppm) 7.64 (d, 1H); 6.66 (s, 1H); 5.14 (d, 1H); 4.43 (s, 2H); 4.02 (m, 1H); 3.5-3.7 (m, 3H); 3.35 (m, 1H).

Example 10

Synthesis of the sodium β-D-xylobioside 6,8-difluoro-7-hydroxycoumarin-4-methanesulfonate substrate (14)

Bromination of the Protected Sugar:

The operating conditions are identical with those used in Example 9 by using aceto-D-xylobiose as the starting product. The obtained acetobromo-α-D-xylobiose is then directly introduced into the following step.

Grafting of the Sugar on the Coumarin:

Under a nitrogen atmosphere and protected from light, 60 mg of coumarin 2 diluted in 5 mL of anhydrous DMF and 5 equivalents of silver carbonate are introduced into a flask. 3 equivalents of acetobromo-α-D-xylobiose are dissolved in 5 mL of anhydrous DMF. The solution is then added very slowly to the previous mixture. After one night of stirring at room temperature, the solution is filtered on celite and the filtrate is evaporated under reduced pressure.

The obtained solid is successively purified twice by chromatography on a silica column (eluent: gradient of 10% MeOH to 20% MeOH in DCM). The compound 13 is obtained pure with a yield of 18%.

$^1$H NMR (MeOD) δ (ppm) 7.70 (d, 1H); 6.61 (s, 1H); 5.38 (d, 1H); 5.16 (m, 3H); 4.92 (m, 1H); 4.78 (m, 2H); 4.32 (s, 2H); 4.18 (m, 1H); 4.10 (m, 1H); 4.03 (m, 1H); 3.54 (m, 2H); 2.09 (m, 15H).

Deprotection of the Functions of the Acetal Type:

Under a nitrogen atmosphere, 27 mg of compound 13 and 7 mL of anhydrous methanol are introduced into a flask. The mixture is cooled to 0° C. and then 200 µL of a 1% (g/g) sodium methylate solution in methanol is added dropwise. The development of the reaction is followed by LC/MS. After 3 hours 30 mins of stirring, some AMBERLITE IR120 is added until neutralization of the medium. After filtration of the AMBERLITE, the filtrate is evaporated under reduced pressure. The residue is taken up in water and the solution is filtered to 0.45 µm, the filtrate is again evaporated under reduced pressure.

The obtained residue is purified with a purification apparatus BIOTAGE-ISOLERAONE (eluent: 5% acetonitrile in pure water, cartridge SNAP C18 12 g, elution flow rate: 3 mL/min).

After evaporation of the solvents, the product 14 is obtained pure with a yield of 40%.

$^1$H NMR (D$_2$O) δ (ppm) 7.56 (d, 1H); 6.58 (s, 1H); 5.11 (d, 1H); 4.40 (d, 1H); 4.36 (s, 2H); 4.10 (m, 1H); 3.91 (m, 1H); 3.82 (m, 1H); 3.7-3.5 (m, 3H); 3.40 (m, 2H); 3.21 (m, 2H).

Example 11

Synthesis of the sodium β-D-xylopolyoside 6,8-difluoro-7-hydroxycoumarin-4-methanesulfonate substrate (16)

Acetylation of xylopolyose, i.e. a Mixture of xylobiose, xylotriose, . . . :

Under a nitrogen atmosphere, 300 mg of xylopolyose, a few grains of 4-dimethylaminopyridine, 28 mL of anhydrous DCM and 9 mL of anhydrous pyridine are introduced into a flask. The mixture is cooled to 0° C. and then 3 mL of acetic anhydride are added dropwise. The medium is then left with stirring for one night. The mixture is then washed 3 times with water, dried on MgSO$_4$ and evaporated under reduced pressure.

Analysis by LC/MS shows that the mixture consists of aceto-xylopolyose with n=1 to 5.

Bromination of the Protected Sugar:

The operating conditions are identical with those used in Example 9 by using 102 mg of aceto-xylopolyose as a starting product. The obtained acetobromo-α-D-xylopolyose is then directly introduced into the next step.

Grafting of the Sugar on the Coumarin:

Under a nitrogen atmosphere and protected from light, 60 mg of coumarin 2 diluted in 5 mL of anhydrous DMF and 5 equivalents of silver carbonate are introduced into a flask. 106 mg of acetobromo-xylopolyose are dissolved in 5 mL of anhydrous DMF. This solution is then very slowly added to the previous mixture. After 36 hours of stirring at room temperature, the solution is filtered on celite and the filtrate is evaporated under reduced pressure.

The obtained solid is finally purified by chromatography on a silica column (eluent: 20% MeOH/80% DCM).

Analysis by LC/MS shows that the mixture consists of the compound 15 with n=0 to 4.

Deprotection of the Functions of the Acetal Type:

Under a nitrogen atmosphere, 10 mg of the compound 15 and 5 mL of anhydrous methanol are introduced into a flask. The mixture is cooled to 0° C. and then 100 μL of a 1% (g/g) sodium methylate solution in methanol is added dropwise. After a few hours of stirring, some AMBERLITE IR120 is added until neutralization of the medium. After filtration of the AMBERLITE, the filtrate is evaporated under reduced pressure in order to obtain the compound 16.

Example 12

Synthesis of the sodium β-D-glucoside 5,6-benzo-7-hydroxycoumarin-4-methanesulfonate substrate (18)

Grafting of the Sugar on the Coumarin:

Under a nitrogen atmosphere and protected from light, 80 mg of coumarin 4 diluted in 6 mL of anhydrous DMF and 5 equivalents of silver carbonate are introduced into a flask. 5 equivalents of acetobromo-α-D-glucose are dissolved in 5 mL of anhydrous DMF. This solution is then added within 45 mins to the previous mixture. After stirring at room temperature, the solution is filtered on celite and the filtrate is evaporated under reduced pressure.

The obtained solid is purified by chromatography on a silica column (eluent: 10% MeOH/90% DCM). The compound 17 is obtained pure with a yield of 37%.

$^1$H NMR (D$_2$O) δ (ppm) 8.04 (d, 1H); 7.50 (d, 1H); 7.25 (m, 2H); 6.56 (s, 1H); 6.31 (s, 1H); 5.30 (m, 2H); 5.08 (m, 1H); 4.96 (d, 1H); 4.56 (d, 1H); 4.26 (m, 1H); 4.21 (s, 2H); 4.03 (m, 1H); 2.10 (m, 12H).

Deprotection of the Functions of the Acetal Type:

Under a nitrogen atmosphere, 60 mg of the compound 17 and 15 mL of anhydrous methanol are introduced into a flask. The mixture is cooled to 0° C. and then 450 μL of a 1% (g/g) sodium methylate solution in methanol is added dropwise. The development of the reaction is followed by LC/MS. After 2 h 50 mins of stirring, some AMBERLITE IR120 is added until neutralization of the medium. After filtration of the AMBERLITE, the filtrate is evaporated under reduced pressure. The residue is taken up in water and the solution is then filtered to 0.45 μm, the filtrate is again evaporated under reduced pressure.

The obtained residue is purified with a purification apparatus BIOTAGE-ISOLERAONE (eluent: 5% acetonitrile in pure water, cartridge SNAP C18 30 g, elution flow rate: 10 mL/min).

After evaporation of the solvents, the product 18 is obtained pure with a yield of 33%.

$^1$H NMR (D$_2$O) δ (ppm) 8.24 (d, 1H); 8.18 (d, 1H); 7.53 (m, 2H); 6.80 (s, 1H); 6.24 (s, 1H); 5.25 (d, 1H); 4.49 (m, 2H); 4.0-3.5 (m, 6H).

Example 13

Synthesis of the sodium β-D-xyloside 5,6-benzo-7-hydroxycoumarin-4-methanesulfonate substrate (20)

Grafting of the Sugar on the Coumarin:

Under a nitrogen atmosphere and protected from light, 55 mg of coumarin 4 diluted 4 mL of anhydrous DMF and 5 equivalents of silver carbonate (0.3 g) are introduced into a flask. 5 equivalents of acetobromo-α-D-xylose (obtained as described in Example 9), are dissolved in 4 mL of anhydrous DMF. This solution is then slowly added to the previous mixture. After 20 h of stirring at room temperature, the solution is filtered on celite and the filtrate is evaporated under reduced pressure.

The obtained solid is purified by chromatography on a silica column (eluent: 10% MeOH/90% DCM). The compound 19 is obtained with a yield of 42%

$^1$H NMR (MeOD/D$_2$O) δ (ppm) 8.57 (d, 1H); 8.00 (d, 1H); 7.68 (t, 1H); 7.55 (t, 1H); 6.89 (s, 1H); 6.52 (s, 1H); 5.53 (m, 1H); 5.31 (m, 2H); 5.08 (m, 1H); 4.61 (m, 2H); 4.23 (m, 1H); 3.78 (m, 1H); 2.17 (m, 9H).

Deprotection of the Functions of the Acetal Type:

Under a nitrogen atmosphere, 40 mg of the compound 19 and 11 mL of anhydrous methanol are introduced into the flask. The mixture is cooled to 0° C. and then 500 μL of a 1% (g/g) sodium methylate solution in methanol is added dropwise. After 2 h 15 mins of reaction, 400 μL of the sodium methylate solution are again added. After 3 h 30 mins of stirring, some AMBERLITE IR120 is added until neutralization of the medium. After filtration of the AMBERLITE, the filtrate is evaporated under reduced pressure.

The obtained residue is purified by reverse phase chromatography on a pre-packed silica column (eluent: 10% acetonitrile in pure water, cartridge PURIFLASH INTERCHROM C18) in order to obtain the compound 20 with a yield of 35%.

¹H NMR (D₂O) δ (ppm) 8.09 (d, 1H); 7.99 (d, 1H); 7.46 (m, 1H); 7.38 (m, 1H); 6.51 (s, 1H); 6.16 (s, 1H); 4.98 (m, 1H); 4.37 (m, 2H); 4.01 (m, 1H); 3.8-3.4 (m, 4H).

Example 14

Synthesis of the sodium β-D-glucoside 7-hydroxy-8-methylcoumarin-4-methanesulfonate substrate (22)

Grafting of the Sugar on the Coumarin:
Under a nitrogen atmosphere and protected from light, 80 mg of coumarin 6 diluted in 7 mL of anhydrous DMF and 5 equivalents of silver carbonate (377 mg) are introduced into a flask. 5 equivalents (563 mg) of acetobromo-α-D-glucose are dissolved in 7 mL of anhydrous DMF. This solution is then slowly added to the previous mixture. After 20 h of stirring at room temperature, the solution is filtered on celite and the filtrate is evaporated under reduced pressure.

The obtained solid is purified once by chromatography on a silica column (eluent: 10% MeOH/90% DCM) and then by reverse phase chromatography on a pre-packed silica column (eluent: gradient from 0% to 50% of acetonitrile in pure water, cartridge PURIFLASH INTERCHROM C18).

The compound 21 is thereby obtained pure with a yield of 17%.
¹H NMR (MeOD) δ (ppm) 7.85 (d, 1H); 7.67 (d, 1H); 6.47 (s, 1H); 5.47 (m, 2H); 5.30 (t, 1H); 5.16 (t, 1H); 4.4-4.1 (m, 5H); 2.25 (s, 3H); 2.08 (m, 12H).

Deprotection of the Functions of the Acetal Type:
Under a nitrogen atmosphere, 18 mg of the compound 21 and 5 mL of anhydrous methanol are introduced into a flask. The mixture is cooled to 0° C. and then 100 μl of a 1% (g/g) sodium methylate solution in methanol is added dropwise. The development of the reaction is followed by TLC. After 1 h 30 mins of stirring, some AMBERLITE IR120 is added until neutralization of the medium. After filtration of the AMBERLITE, the filtrate is evaporated under reduced pressure.

The compound 22 is obtained with a yield of 34%.
¹H NMR (D₂O) δ (ppm) 7.53 (d, 1H); 7.06 (d, 1H); 6.26 (s, 1H); 5.15 (d, 1H); 4.24 (m, 2H); 3.90 (m, 1H); 3.73 (m, 1H); 3.6-3.4 (m, 4H); 2.13 (s, 3H).

Example 15

Synthesis of the sodium β-D-galactoside 7-hydroxy-8-methylcoumarin-4-methanesulfonate substrate (24)

Grafting of the Sugar on the Coumarin:
Under a nitrogen atmosphere and protected from light, 80 mg of coumarin 6 diluted in 5 mL of anhydrous DMF and 5 equivalents of silver carbonate (377 mg) are introduced into a flask. 5 equivalents (563 mg) of acetobromo-α-D-galactose are dissolved in 5 mL of anhydrous DMF. This solution is then slowly added to the previous mixture. The development of the reaction is followed by TLC. After 40 h of stirring at room temperature, the solution is filtered on celite and the filtrate is evaporated under reduced pressure.

The obtained solid is purified once by reverse phase chromatography on a pre-packed silica column (eluent: gradient from 0% to 50% of acetonitrile in pure water, cartridge PURIFLASH INTERCHROM C18) and then by chromatography on a silica column (eluent: 10% MeOH/90% DCM). The compound 23 is thus obtained pure with a yield of 42%.

¹H NMR (MeOD) δ (ppm) 7.81 (d, 1H); 7.65 (d, 1H); 6.45 (s, 1H); 5.49 (m, 3H); 5.37 (m, 1H); 4.37 (m, 3H); 4.20 (m, 2H); 2.23 (s, 3H); 2.19 (s, 3H); 2.12 (s, 3H); 2.08 (s, 3H); 2.03 (s, 3H).
¹³C NMR (MeOD) δ (ppm) 170.80; 170.65; 170.08; 169.97; 161.57; 157.33; 152.52; 148.64; 124.58; 114.82; 114.41; 114.15; 110.77; 98.48; 70.93; 70.67; 68.60; 67.39; 61.29; 52.61; 19.41; 19.37; 19.19; 19.18; 7.03.

Deprotection of the Functions of the Acetal Type:
Under a nitrogen atmosphere, 45 mg of the compound 23 and 20 mL of anhydrous methanol are introduced into the flask. The mixture is cooled to 0° C. and then 300 μL of a 1% (g/g) sodium methylate solution in methanol is added dropwise. The development of the reaction is followed by TLC. After 1 h 30 mins of stirring, the reaction is not complete, 300 μL of the methylate solution are again added. After 3 h of reaction, some AMBERLITE IR120 is added until neutralization of the medium. After filtration of the AMBERLITE, the filtrate is evaporated under reduced pressure.

The compound 24 is obtained with a yield of 36%.
¹H NMR (D₂O) δ (ppm) 7.51 (d, 1H); 7.07 (d, 1H); 6.24 (s, 1H); 5.09 (d, 1H); 4.0-3.6 (m, 8H); 2.13 (s, 3H).

The thereby obtained substrates notably find their application for detecting glycosidase activities (EC3.2.1) on enzymatic extracts either purified or not or on microorganisms or on cells.

For example, it will be possible to carry out the fluorescent assay of xylanase and/or cellulase and/or cellobiase and/or glucosidase and/or xylosidase and/or galactosidase activities of enzymatic extracts, or else carry out the screening by fluorescence according to their glycosidase activities (EC3.2.1) of enzymes or of microorganisms or cells.

More particularly, the novel substrates according to the invention will allow detection of glycosidase activities (EC3.2.1) on enzymatic extracts either purified or not or on microorganisms or on cells compartmented in aqueous droplets in suspension in an oil phase (emulsion) produced by mechanical stirring. It will thus be possible to carry out screening by FACS (Fluorescence Activated Cell Sorting) according to their xylanase and/or cellulase and/or cellobiase and/or glucosidase and/or xylosidase and/or galactosidase activities of enzymes or microorganisms or cells compartmented in aqueous droplets in suspension in an oil phase.

Still more particularly, the substrates according to the invention will allow the detection of glycosidase activities (EC3.2.1) on enzymatic extracts either purified or not or on microorganisms or on cells compartmented in aqueous droplets in suspension in an oil phase (emulsion) produced by a microfluidic device. With this assumption, it will be possible for example to carry out screening according to their xylanase and/or cellulase and/or cellobiase and/or glucosidase and/or xylosidase and/or galactosidase activities of enzymes or microorganisms or cells compartmented in aqueous droplets in suspension in an oil phase generated by a microfluidic device.

Different examples of detections of enzymatic activities by means of the described fluorogenic substrates will now be given, as an indication and by no means as a limitation.

Example 16

Detection of Enzymatic Activities on Soluble Enzymatic Extracts with the Substrates 10, 12, 14 and 18

Figure 2:
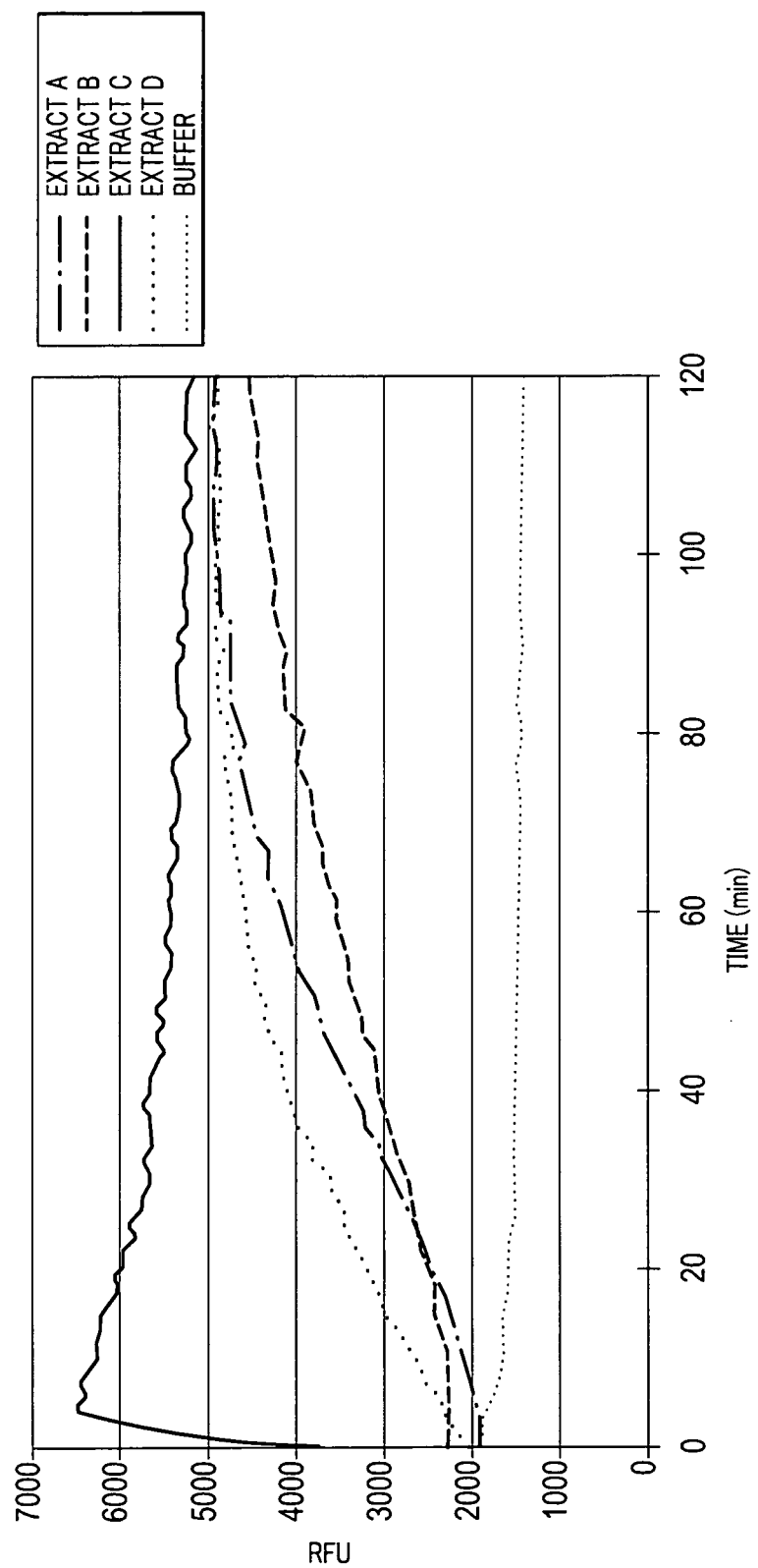
FIG. 2 shows detection of enzymatic activies on the soluble extracts of enzymes with the substrate 18.

The enzymatic kinetics are achieved in a microplate on soluble enzymatic extracts (A, B, C and D) rich in activities of the cellulase and xylanase type. These extracts are diluted 10 times (substrate 18, FIG. 1) or 100 times (substrate 10, 12 and 14, FIG. 2) in a 50 mM phosphate buffer, NaCl 150 mM, pH=7.5. A volume of 20 μL of diluted enzymatic extract is added to 20 μL of fluorogenic substrate (10, 12, 14 or 18) at 0.25 mM in a 50 mM phosphate buffer, NaCl 150 mM, pH=7.5. The kinetics are achieved at 30° C. The enzymatic hydrolysis of the different fluorogenic substrate is followed for 120 minutes by measuring the fluorescence with excitation and emission wavelengths of: 339 nm and 452 nm for the substrates 10, 12 and 14; 375 nm and 510 nm for the substrate 18.

The obtained results (FIGS. 1 and 2) show that the tested fluorogenic substrates allow detection of the enzymatic activities of type β-glucosidase (substrates 10 and 18), β-xylosidase (substrate 12) and xylanase type (substrate 14) in the enzymatic extracts used.

Example 17

Detection of Enzymatic Activities on Microorganisms with the Fluorogenic Substrates 8 and 10

Different control strains are cultivated in an LB medium at 30° C. with stirring (240 rpm) for 18 h. For each strain, the culture is centrifuged (2,500 g, 5 min) and the pellet of cells is washed twice in 5 mL of LB medium (centrifugation at 2,500 g, 5 min). This pellet is used for inoculating at OD=0.005 a culture in an inducing medium (Dubos medium with 2.5 g/L of carboxymethyl-cellulose) containing the fluorogenic substrate (8 or 10) at 0.25 mM. The culture is incubated at 30° C. without stirring for 24 h. Culture supernatant samples are taken at different incubation times in order to be able to follow the occurrence of cellulase or β-glucosidase activities in the culture medium. The occurrence of these activities is followed by measurement of the fluorescence on the culture supernatants in microplates with excitation and emission wavelengths of 388 nm and 455 nm.

Figure 3:
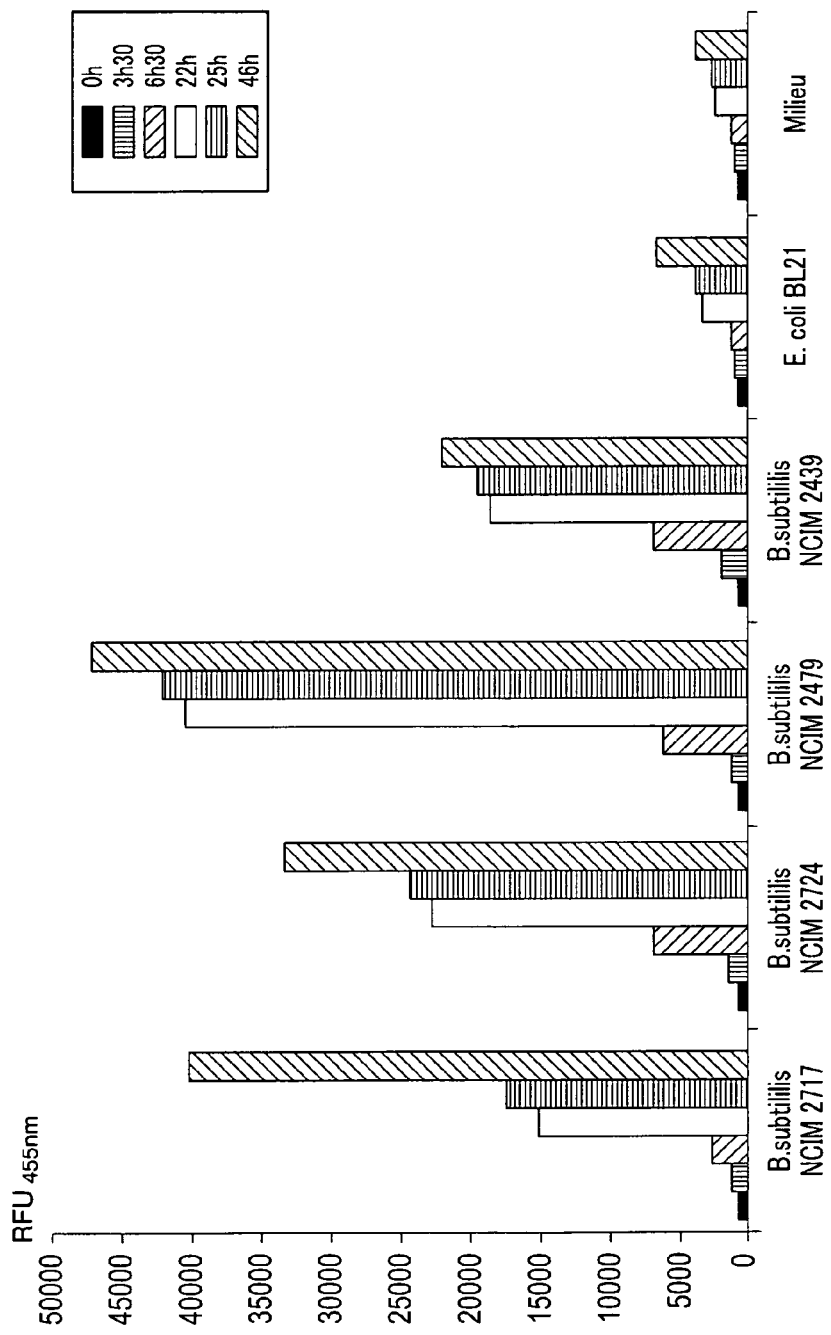
FIG. 3 shows glucosidase activity measurement on microorganisms with the fluorogenic substrate 10.
Figure 4:
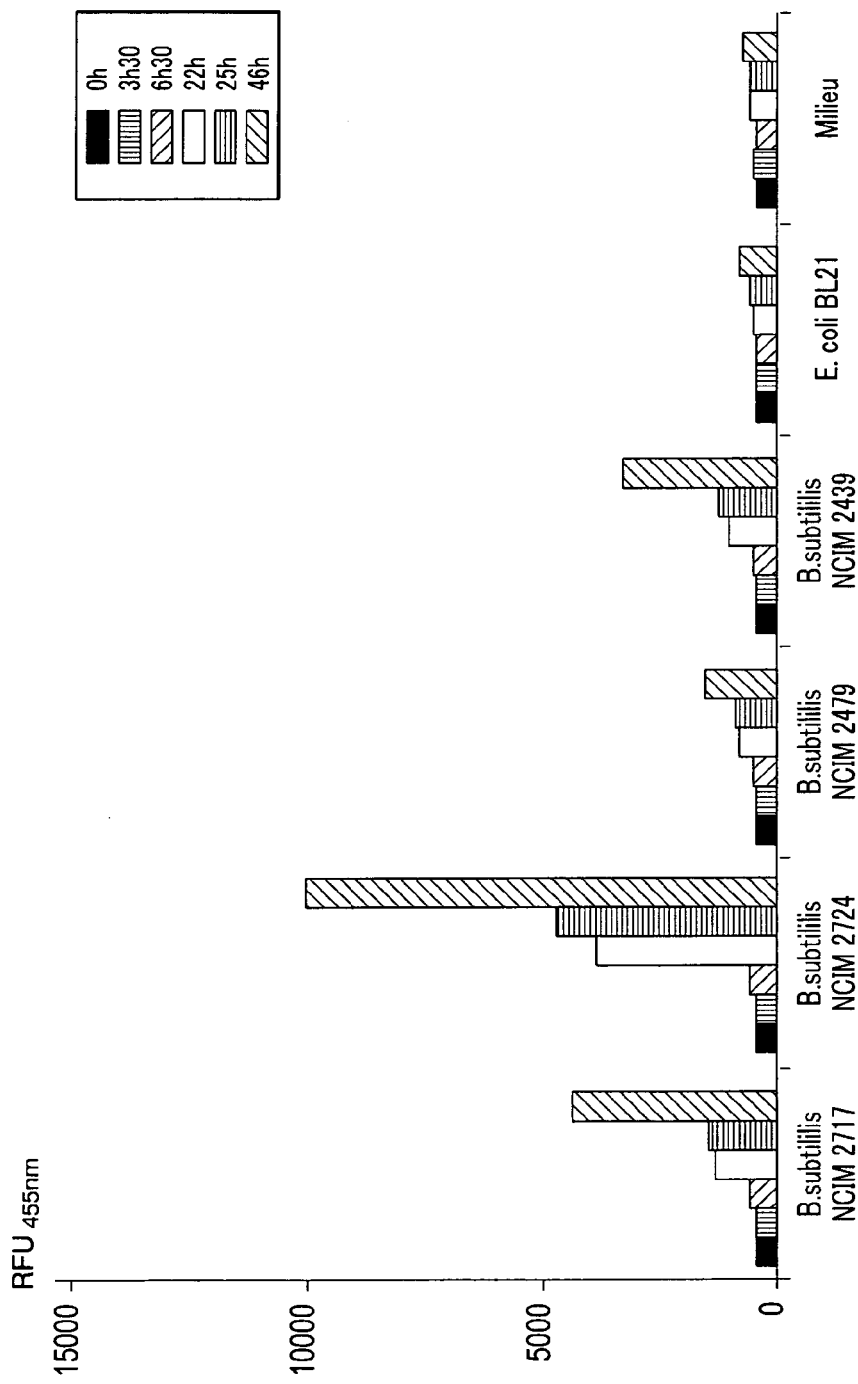
FIG. 4 shows cellulase activity measurement on microorganisms with the fluorgenic substrate 8.

The obtained results (FIGS. 3 and 4) show that the tested fluorogenics substrates allow detection of the enzymatic activities of the β-glucosidase type (substrate 10) and cellulase type (substrate 8) on cultures of microorganisms.

Example 18

Detection of Cellulase Activity on Microorganisms in Emulsion with the Substrate 8

Two control stains are used: one having a cellulase activity (*Bacillus subtilis* NCIM 2724) the other one not having any activity (*Escherichia coli* BL21). Both strains are cultivated in an LB medium at 30° C. with stirring (240 rpm) for 18 h. For each strain, the culture is centrifuged (2 500 g, 5 min) and the pellet of cells is washed twice in 5 mL of an LB medium (centrifugation at 2 500 g, 5 min). This pellet is used for inoculation at OD=0.005 a culture in an inducing medium (Dubos medium with 2.5 g/L of carboxymethyl-cellulose) containing the fluorogenic substrate 8 and 2.5 μM (*B. subtilis* NCIM 2724) or 10 μM (*E. coli* BL21) of sulforhodamine. Both of these cell suspensions are used with perfluorinated oil in order to produce an emulsion consisting of two populations of droplets each containing one of the described suspensions. The blue and red fluorescences of the droplets are measured individually, on a sample of the emulsion, during production (t=0 h) and reinjection after having incubated the emulsion for 24 h at 30° C.

Figure 5A:
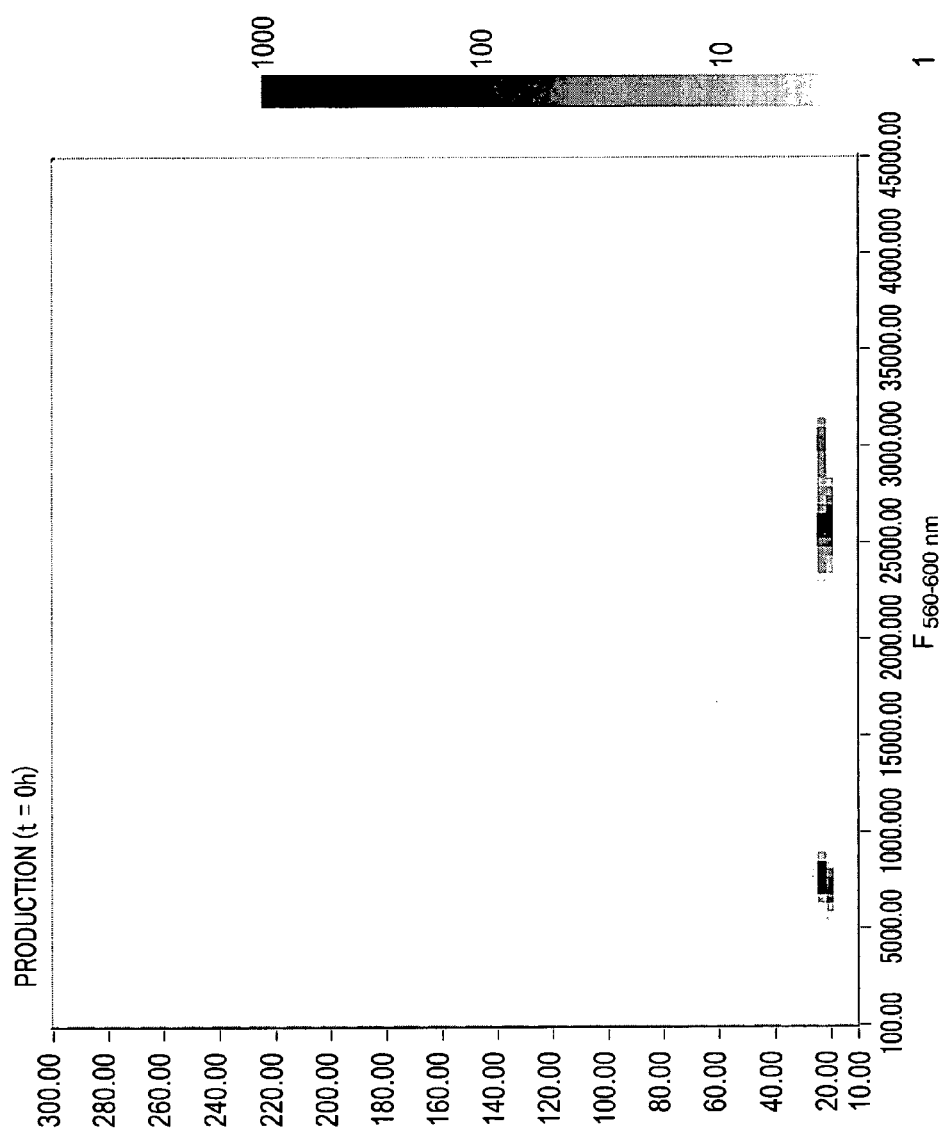
FIG. 5 shows cellulase activity tests on microorganisms in an emulsion with the substrate 8.
Figure 5B:
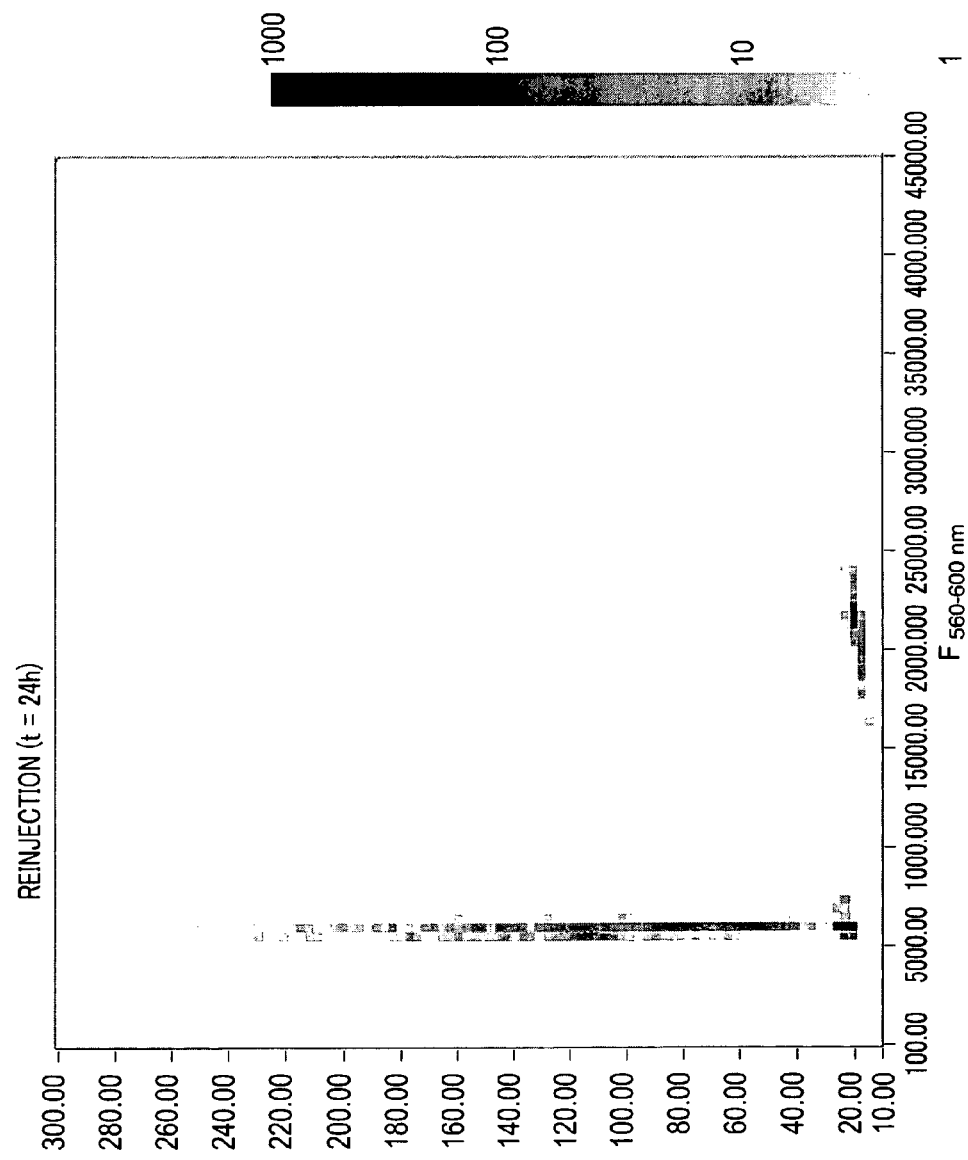

The graphs a and b, shown in FIG. 5, are two dimensional histograms of the red (in abscissas, RFU) and blue (in ordinates, RFU) fluorescence intensities measured on the emulsion during its production (a) and its reinjection after incubation fro 24 h at 30° C. (b). The population density is illustrated by a color code varying from pink (1 droplet) to red (>1,000 droplets) according to a logarithmic scale. Two populations of droplets are observable: one with low red fluorescence containing *Bacillus subtilis* NCIM 2724 (active strain) and 2.5 μM of sulforhodamine, the other one with intense red fluorescence containing *Escherichia coli* BL21 (inactive strain) and 10 μM of sulforhodamine). The statistical analysis of these histograms is shown in Table 1.

TABLE 1

Statistical analysis of the droplet populations during the cellulose activity test on microorganisms in an emulsion with a substrate 8

| | | 2.5 μM | 10 μM |
|---|---|---|---|
| | [sulforhodamine] | *B. subtilis* | *E. coli* |
| | Identity of the strains | NCIM 2724 | BL21 |
| Production (t = 0 h) | Number of analyzed drops | 16.083 | |
| | Average red fluorescence (RFU) | 6.434 ± 387 | 25.775 ± 825 |
| | Average blue fluorescence (RFU) | 18.78 ± 1.19 | |
| | Detection threshold of positive droplets (RFU) | 37.56 | |
| Reinjection (t = 24 h) | Number of analyzed drops | 15.869 | |
| | % of positive droplets | 27.61% | 0.26% |

The droplets containing the active strain (*Bacillus subtilis* NCIM 2724) see their blue fluorescence significantly increased after 24 h of incubation (FIG. 5). Conversely, the droplets containing the inactive strain (*Escherichia coli* BL21) do not have any increase of their blue fluorescence. For the active strain (*Bacillus subtilis* NCIM 2724), 27% of the droplets are identified as positive, against 0.29% for the inactive strain (*Escherichia coli* BL21). As a conclusion, the substrate 8 allows detection of an activity of the cellulase type on microorganisms within an emulsion generated by a microfluidic system.

The invention claimed is:

1. A substituted sulfonated coumarin of formula (I)

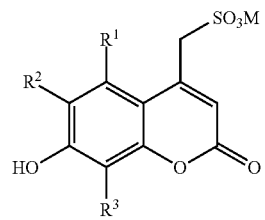

wherein:
$R^1$ represents H, or OH, or a linear or branched $C_1$-$C_6$ alkyl radical, either substituted or not,
$R^2$ represents H, or a linear or branched $C_1$-$C_6$ alkyl radical, either substituted or not,
$R^1$ and $R^2$ may form together a ring, either substituted or not,
$R^3$ represents H, or a linear or branched $C_1$-$C_6$ alkyl radical, either substituted or not, and
M represents Na or K.

2. The coumarin according to claim 1, wherein said coumarin is sodium 5,6-benzo-7-hydroxycoumarin-4-methanesulfonate.

3. A method for obtaining coumarin according to claim 2, comprising purifying the coumarin by reverse phase absorption chromatography on a silica column.

4. The coumarin according to claim 1, wherein said coumarin is sodium 7-hydroxy-8-methylcoumarin-4-methanesulfonate.

5. A method for obtaining coumarin according to claim 4, comprising purifying the coumarin by reverse phase absorption chromatography on a silica column.

6. A method of making a substituted coumarin, sodium 5,6-benzo-7-hydroxycoumarin-4-methanesulfonate, comprising reacting ethyl 4-chloroacetoacetate with 1,3-dihydroxynaphthalene, in methane sulfonic acid, and then reacting sodium sulfite with the thereby obtained product.

7. The method according to claim 6, further comprising purifying the thus obtained substituted coumarin product by reverse phase absorption chromatography on a silica column.

8. A method of making a substituted coumarin, sodium 7-hydroxy-8-methylcoumarin-4-methanesulfonate, comprising reacting ethyl 4-chloroacetoacetate with 2-methylresorcinol, in methane sulfonic acid and then reacting sodium sulfite with the thereby obtained product.

9. The method according to claim 8, further comprising purifying the thus obtained substituted coumarin product by reverse phase absorption chromatography on a silica column.

10. A fluorogenic substrate where a sugar is covalently bonded to the 7-hydroxy position of a substituted coumarin sulfonated fluorophore selected from the group consisting of: sodium β-D-glucoside 5,6-benzo-7-hydroxycoumarin-4-methanesulfonate, sodium β-D-xyloside 5,6-benzo-7-hydroxycoumarin-4-methanesulfonate, sodium β-D-glucoside 7-hydroxy-8-methylcoumarin-4-methanesulfonate; and sodium β-D-galactoside 7-hydroxy-8-methylcoumarin-4-methanesulfonate.

11. A method of making a substrate according to claim 10, comprising covalently bonding the sugar moiety to the 7-hydroxy position of the corresponding 7-hydroxy substituted coumarin sulfonated fluorophore by reaction in DMF.

12. A method of detecting glycosidase activities (EC3.2.1) from enzymatic extracts, either purified or not, or from microorganisms or cells, comprising contacting said extracts, microorganisms or cells with one of the fluorogenic substrates according to claim 10.

13. The method according to claim 12, wherein said extracts or microorganisms or cells are compartmented in aqueous droplets in suspension in an oil phase.

14. The method according to claim 13, wherein said aqueous droplets are produced by a micro fluidic device.

* * * * *